United States Patent
Formolo

(10) Patent No.: US 11,041,384 B2
(45) Date of Patent: Jun. 22, 2021

(54) METAL ISOTOPE APPLICATIONS IN HYDROCARBON EXPLORATION, DEVELOPMENT, AND PRODUCTION

(71) Applicant: Michael J. Formolo, The Woodlands, TX (US)

(72) Inventor: Michael J. Formolo, The Woodlands, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 680 days.

(21) Appl. No.: 15/900,180

(22) Filed: Feb. 20, 2018

(65) Prior Publication Data

US 2018/0245464 A1    Aug. 30, 2018

Related U.S. Application Data

(60) Provisional application No. 62/464,853, filed on Feb. 28, 2017.

(51) Int. Cl.
*E21B 49/08* (2006.01)
*G01N 33/24* (2006.01)
*E21B 49/00* (2006.01)
*E21B 47/11* (2012.01)

(52) U.S. Cl.
CPC .............. *E21B 49/08* (2013.01); *E21B 47/11* (2020.05); *E21B 49/00* (2013.01); *G01N 33/241* (2013.01); *E21B 49/0875* (2020.05)

(58) Field of Classification Search
CPC .......... E21B 49/08; E21B 47/11; E21B 49/00; E21B 49/0875; E21B 49/02; G01N 33/241; G01N 33/15
See application file for complete search history.

(56) References Cited

U.S. PATENT DOCUMENTS

| | | | |
|---|---|---|---|
| 4,560,664 A | 12/1985 | Demaison et al. | |
| 4,833,915 A | 5/1989 | Radd et al. | |
| 5,388,456 A | 2/1995 | Kettel | |
| 6,509,566 B1 | 1/2003 | Wamsley et al. | |

(Continued)

FOREIGN PATENT DOCUMENTS

| | | |
|---|---|---|
| WO | WO 2007/008932 A2 | 1/2007 |
| WO | WO 2013/148442 A1 | 10/2013 |

OTHER PUBLICATIONS

G Todd Ventura "The stable isotope composition of vanadium, nickel, and molybdenum in crude oils" 15 Aptile 2015 (Year: 2015).*

(Continued)

*Primary Examiner* — Regis J Betsch
*Assistant Examiner* — Kaleria Knox
(74) *Attorney, Agent, or Firm* — ExxonMobil Upstream Research Company, Law Department

(57) ABSTRACT

Described herein are methods and techniques for utilizing a multiple metal isotope signature as an internal tracers for hydrocarbon source, alteration, and mixing. The multiple metal isotope signature may comprise a ratio of a at least two isotopes of a first metal, a ratio of at least two isotopes of a second metal, and a ratio of at least two isotopes of a third metal from a sample. The isotope ratios of the first, second, and third metal may be integrated to form the multiple metal isotope signature.

24 Claims, 5 Drawing Sheets

(56) References Cited

U.S. PATENT DOCUMENTS

| | | | |
|---|---|---|---|
| 6,645,769 | B2 | 11/2003 | Tayebi et al. |
| 6,810,332 | B2 | 10/2004 | Harrison |
| 6,888,127 | B2 | 5/2005 | Jones et al. |
| 6,985,841 | B2 | 1/2006 | Barroux |
| 7,011,154 | B2 | 3/2006 | Maher et al. |
| 7,124,030 | B2 | 10/2006 | Ellis |
| 7,174,254 | B2 | 2/2007 | Ellis |
| 7,210,342 | B1 | 5/2007 | Sterner et al. |
| 7,297,661 | B2 | 11/2007 | Beyer et al. |
| 7,337,660 | B2 | 3/2008 | Ibrahim et al. |
| 7,387,021 | B2 | 6/2008 | DiFoggio |
| 7,395,691 | B2 | 7/2008 | Sterner et al. |
| 7,529,626 | B1 | 5/2009 | Ellis |
| 7,571,644 | B2 | 8/2009 | Ibrahim et al. |
| 7,704,746 | B1 | 4/2010 | White et al. |
| 7,821,635 | B2 | 10/2010 | Pope et al. |
| 8,316,934 | B2 | 11/2012 | Pietrobon |
| 8,355,872 | B2 | 1/2013 | Rowan |
| 8,492,153 | B2 | 7/2013 | Jones et al. |
| 8,505,375 | B2 | 8/2013 | Smalley |
| 8,577,613 | B2 | 11/2013 | Bryant et al. |
| 8,714,246 | B2 | 5/2014 | Pop et al. |
| 9,128,076 | B2 | 9/2015 | Lamberti et al. |
| 9,146,225 | B2 | 9/2015 | Pottorf et al. |
| 9,243,466 | B2 | 1/2016 | Klomp et al. |
| 9,594,879 | B2 | 3/2017 | Eiler |
| 9,612,231 | B2 | 4/2017 | Pottorf et al. |
| 9,697,338 | B2 | 7/2017 | Eiler et al. |
| 2002/0120429 | A1 | 8/2002 | Ortoleva |
| 2008/0040086 | A1 | 2/2008 | Betancourt et al. |
| 2008/0049140 | A1 | 2/2008 | Kim et al. |
| 2008/0147326 | A1 | 6/2008 | Ellis |
| 2009/0071239 | A1 | 3/2009 | Rojas et al. |
| 2010/0086180 | A1 | 4/2010 | Wallace |
| 2010/0257004 | A1 | 10/2010 | Perlmutter et al. |
| 2011/0250582 | A1 | 10/2011 | Gates et al. |
| 2012/0123582 | A1* | 5/2012 | Jasper ............ G01N 33/15 700/107 |
| 2012/0134749 | A1 | 5/2012 | Darrah |
| 2014/0182840 | A1 | 7/2014 | Sheehy et al. |
| 2014/0250999 | A1* | 9/2014 | Lawson ............ E21B 49/02 73/152.23 |
| 2014/0288853 | A1 | 9/2014 | Dreyfus et al. |
| 2014/0303895 | A1 | 10/2014 | Dreyfus et al. |
| 2014/0378319 | A1 | 12/2014 | Regberg et al. |
| 2015/0127313 | A1 | 5/2015 | Lawson et al. |
| 2016/0258922 | A1 | 9/2016 | Formolo et al. |

OTHER PUBLICATIONS

Christopher Siebert "Determination of molybdenum isotope fractionation by double-spike multicollector inductively coupled plasma mass spectrometry" Jul. 3, 2001 (Year: 2001).*

Georgiev et al. (2016) "Re-Os dating of maltenes and asphaltenes within single samples of crude oil", Geochimica et Cosmochimica Acta, Pergamon Press, New York, NY, vol. 179, Jan. 29, 2016, pp. 53-75; XP029463301A, ISSN: 0016-7037, DOI: 10.1016/J.GCA. 2016.01.016.

Worden et al. (2000) "The origin and production geochemistry of radioactive lead ($^{210}$Pb) in NORM-contaminated formation waters", Journal of Geochemical Exploration, Elsevier, Amsterdam, NL, vol. 69-70, Jun. 2000, pp. 695-699; XP027188964, ISSN: 0375-6742.

Yasnygina et al. (2015) "Trace Elements and Sr Isotopes in the Crude Oils from the Sakhalin Offshore Fields", Russian Journal of Pacific Geology, Pleiades Publishing, Moscow, vol. 9, No. 2, Apr. 14, 2015, pp. 109-119; XP035481681, ISSN: 1819-7140, DOI: 10.1134/S1819714015020074.

Aeschbach-Hertig et al. (2000) "Palaeotemperature reconstruction from noble gases in ground water taking into account equilibration with entrapped air", Nature, vol. 405, pp. 1040-1044.

Al-Shahristani et al. (1972), "Vertical Migration of Oil in Iraqi Oil Fields: Evidence based on Vanadium and Nickel Concentrations", Geochimica et Cosmochimica Acta, vol. 36, Issue 9, pp. 929-938.

Ballentine et al. (2002) "Production, Release and Transport of Noble Gases in the Continental Crust", Ch. 12, pp. 481-538.

Ballentine et al. (2002) "Tracing Fluid Origin, Transport and Interaction in the Crust", Ch. 13, pp. 539-614.

Barwise (1990), "Role of Nickel and Vanadium in Petroleum Classification", Energy & Fuels, vol. 4, pp. 647-652.

Berner et al. (1988) "Maturity related mixing model for methane, ethane and propane, based on carbon isotopes", Org. Geochem., vol. 13, Nos. 1-3, pp. 67-72.

Bigeleisen et al. (1947) "Calculation of Equilibrium Constants for Isotopic Exchange Reactions", The Journal of Chemical Physics, vol. 15, No. 5, pp. 261-267.

Burnham et al. (1989) "A chemical kinetic model of vitrinite maturation and reflectance", Geochimica et Cosmochimica Acta, vol. 53, Issue 10, pp. 2649-2657.

Camilli et al. (2007) "Characterizing Marine Hydrocarbons with In-Situ Mass Spectrometry", IEEE/MTS Oceans (IEEE/MTS, Vancouver Canada 2007), pp. 1-7.

Casey et al. (2015) "Analysis of low abundance trace metals and $^{15}$V/$^{50}$V isotope ratios in crude oils: New methods for characterization and exploration", Goldschmidt Abstracts.

Chung et al. (1979) "Use of stable carbon isotope compositions of pyrolytically derived methane as maturity indices for carbonaceous materials", Geochimica et Cosmochimica Acta, vol. 43, Issue 12, pp. 1979-1988.

Crovetto et al. (1982) "Solubilities of inert gases and methane in H2O and D2O in the temperature range of 300 to 600K", Journal of Chemical Physics, 76(2), pp. 1077-1086.

Hassanzadeh et al. (2011) "Petroleum System Analysis Using Geochemical Studies, Isotope and 1D Basin Modeling in Hendijan Oil Field, SW Iran", International Petroluem Technology Conference IPTC 14797, p. 1-11.

Hohl et al. (2010), "Energy, Environment and Climate Directorate White Paper", DCO Energy, Environment and Climate Workshop, pp. 1-38.

Huc (2003), "Petroleum Geochemistry at the Dawn of the 21st Cenruy", Oil & Gas Science and Technology—Rev. Ifp., vol. 58, No. 2, pp. 233-241.

Irrgeher et al. (2016), "Application of non-traditional stable isotopes in analytical ecogeochemistry assessed by MC ICP-MS—A critical review", Analytical and Bioanalytical Chemistry, vol. 408, Issue 2, pp. 369-385.

James (1990) "Correlation of Reservoired Gases Using the Carbon Isotopic Compositions of Wet Gas Components", The American Association of Petroleum Geologists Bulletin, vol. 74, No. 9, pp. 1441-1458.

Larter et al. (1995), "Reservoir geochemistry: methods, applications and opportunities", Geolgoical Society of London Special Publication No. 86, pp. 5-32.

Lewan (1984), "Factors Controlling the Proportionality of Vanadium to Nickel in Crude Oils", Geochimica et Cosmochimica Acta, vol. 48, Issue 11, pp. 2231-2238.

Liu et al. (2007), "Ternary Geochemical-Tracing System in Natural Gas Accumulation", Science in China Series D-Earth Sciences, vol. 50, No. 10, pp. 1494-1503.

Liu et al. (2010) "On the proper use of the Bigeleisen-Mayer equation and corrections to it in the calculation of isotopic fractionation equilibrium constants", Geochimica et Cosmochimica Acta, vol. 74, pp. 6965-6983.

Lopez et al. (1995) "V/Ni ratio in maltene and asphaltenes fractions of crude oil from the west Venezuelan Basin: correlation studies", Chemical Geology, vol. 119, pp. 225-262.

Magoon et al. (1994) "The Petroleum System—From Source to Trap", AAPG Memoir 60, pp. 3-24.

Prinzhofer et al. (2003), "Gas Isotopes Tracing: An Important Tool for Hydrocarbons Exploration", Oil & Gas Science and Technology—Rev. IFP, vol. 58, No. 2, pp. 299-311.

Ratié et al. (2016), "Nickel Isotope Fractionation During Laterite Ni Ore Smelting and Refining: Implications for Tracing the Sources of Ni in Smelter-Affected Soils", Applied Geochemistry, vol. 64, pp. 136-145.

(56) References Cited

OTHER PUBLICATIONS

Richet et al. (1977) "A Review of Hydrogen, Carbon, Nitrogen, Oxygen, Sulphur, and Chlorine Stable Isotope Fractionation Among Gaseous Molecules", *Annual Review of Earth and Planetary Science*, pp. 65-110.
Rustad et al. (2007) "Ab Initio Calculation of Isotopic Fractionation in B(OH)3(aq) and BOH4-(aq)", *Journal of American Chemical Societ*, vol. 129, pp. 2222-2223.
Rustad et al. (2010) "Calculation of boron-isotope fractionation between $B(OH)_3$(aq) and $B(OH)_4$-(aq)", Science Direct, *Geochimica et Cosmochimica Acta*, vol. 74, Issue 10, pp. 2843-2850.
Sasaki et al. (1998) "Vanadium as an internal marker to evaluate microbial degradation of crude oil", *Environmental Science and Technology*, vol. 32, pp. 3618-3621.
Stolper et al. (2014) "Combined $^{13}$C-D and D-D clumping in methane: Methods and preliminary results", Science Direct, *Geochimica et Cosmochimica Acta*, vol. 126, pp. 169-191.
Stolper et al. (2014) "Formation temperatures of thermogenic and biogenic methane", *Science*, vol. 344, Issue 6191, pp. 1500-1503.
Stolper et al. (2015) "Distinguishing and understanding thermogenic and biogenic sources of methane using multiply substituted isotopologues", Science Direct, *Geochimica et Cosmochimcia Acta*, vol. 161, pp. 219-247.
Sudararaman et al. (1988) "Vanadylporphyrins, indicators of kerogen breakdown and generation of petroleum", *Geochimica et Cosmochimica Acta*, vol. 52, pp. 2337-2341.
Sweeney et al. (1990) "Evaluation of a Simple Model of Vitrinite Reflectance Based on Chemical Kinetics", *The American Association of Petroleum Geologists Bulletin*, vol. 74, No. 10, pp. 1559-1570.
Torgersen et al. (1999) "Air-Xe enrichments in Elk Hills oil field gases: role of water in migration and storage", *Earth and Planetary Science Letters*, vol. 167, pp. 239-253.
Urey et al. (1933) "Some Thernodynamic Properties of the H1H2, H2H2 Molecules and Compounds Containing the H2 Atom", *Journal of Chemical Physics*, vol. 1, pp. 137-143.
Ventura et al. (2015) "The stable isotope composition of vanadium, nickel, and molybdenum in crude oils", *Applied Geochemistry*, vol. 59, pp. 104-117.
Wang et al. (2009) "Equilibrium 2H/1H fractionations in organic molecules: I. Experimental calibration of ab initio calculations", ScienceDirect, *Geochimica et Cosmochimica Acta*, vol. 73, pp. 7060-7075.
Wang et al. (2015) "Nonequilibirum clumped isotope signals in microbial methane", *Science*, vol. 348, Issue 6233, pp. 428-431.
Webb et al. (2013) "Position-Specific and Clumped Stable Isotope Studies: Comparison of the Urey and Path-Integral Approaches for Carbon Dioxide, Nitrous Oxide, Methane, and Propane", *The Journal of Physical Chemistry*, vol. 118, pp. 467-474.
Whiticar, M.J. (1996) "Stable isotope geochemistry of coals, humic kerogens and related natural gases", *International Journal of Coal Geology*, vol. 32, pp. 191-215.
Wu et al. (2016), "Vanadium isotope measurement by MC-ICP-MS", *Chemical Geology*, vol. 421, pp. 17-25.

\* cited by examiner

METAL ISOTOPE APPLICATIONS IN HYDROCARBON EXPLORATION, DEVELOPMENT, AND PRODUCTION

CROSS REFERENCE TO RELATED APPLICATIONS

This application claims the benefit of U.S. Provisional Application No. 62/464,853, filed on Feb. 28, 2017, the entirety of which is incorporated herein by reference.

FIELD OF THE INVENTION

Described herein are methods and systems that utilize metal isotope signatures to enhance hydrocarbon exploration, development, and production processes.

BACKGROUND

Hydrocarbons are generated in the subsurface from source rocks rich in organic matter. Following initial deposition, source rocks are buried and subject to increasing temperature and pressure with increasing burial. Hydrocarbons are then generated when the source rocks reach temperatures sufficient for thermal conversion of organic matter to kerogen and then to free liquid and/or gaseous hydrocarbon phases in a process called source rock maturation. Upon generation, the hydrocarbons may subsequently be expulsed from the source rock and migrated in the subsurface to reservoir rocks (such as sandstones or limestones) that have sufficient porosity, structure, and an adequate seal that make them capable of trapping the hydrocarbon phase(s), allowing hydrocarbons to accumulate. Alternatively, hydrocarbons may migrate to a surface location (e.g., a seep). Any hydrocarbons present in the subsurface may be preserved or they may be subjected to different forms of alteration. For example, biodegradation is the process of degradation or consumption of hydrocarbons by microorganisms. Similarly, hydrocarbons may be thermally altered by exposure to temperatures above their thermal stability. Alternatively, hydrocarbons may be oxidized or consumed in processes, such as thermochemical sulfate reduction.

Conventional hydrocarbon exploration, development, and production practices use molecular geochemistry analysis, stable isotope analysis, and metal concentration analysis of hydrocarbon compounds in oil and gas samples. These techniques are used to attempt to estimate the maturity of the source rock from which the hydrocarbons were generated, the source facies from which the hydrocarbons were generated (e.g., marine or terrestrial source rocks), and can sometimes be used to differentiate between different potential origins of hydrocarbons (e.g., biogenic or thermogenic) or provide information on hydrocarbon alteration.

For example, conventional methods have taken advantage of the high concentrations of transition metals, such as vanadium (V), nickel (Ni), iron (Fe), and to a lesser extent molybdenum (Mo), chromium (Cr), cobalt (Co), zinc (Zn), and copper (Cu), found in crude oils to attempt to formulate tracers for hydrocarbon source. In a typical method, a single metal isotope signature (e.g., a single isotope of V or Ni) is measured in combination with the ratio of metal concentrations of interest (e.g., V/(V+Ni)). For example, the concentration and chemical speciation of vanadium in hydrocarbons has been used to provide information regarding source rock deposition (see e.g., M. D. Lewan, "Factors Controlling the Proportionality of Vanadium to Nickel in Crude Oils", Geochimica et Cosmochimica Acta, Vol. 48, pp. 2231-2238 (1984)), petroleum generation (see e.g., Sundararaman et al. (1988)), oil migration (see e.g., Al-Shahristani et al., "Vertical Migration of Oil in Iraqi Oil Fields: Evidence Based on Vanadium and Nickel Concentrations", Geochimica et Cosmochimica Acta, Vol. 36, pp. 929-938 (1972)), oil biodegradation (see e.g., Sasaki et al., "Vanadium as an internal marker to evaluate microbial degradation of crude oil" Environmental Science and Technology, Vo. 22, pp. 3618-3621, (1998)), reservoir connectivity (see e.g., López et al., "V/Ni ratio in maltene and asphaltene fractions of crude oil from the west Venezuelan Basin: correlation studies", Chemical Geology, Vol. 119, pp. 225-262 (1995)), and oil-source rock correlations (see e.g., A. J. G. Barwise, "Role of Nickel and Vanadium in Petroleum Classification", Energy & Fuels, Vol. 4, pp. 647-652 (1990)).

However, such conventional methods often cannot provide the level of detail needed to support evidence linking source rocks to oils, oils to oils, and in deciphering mixtures of oils. That is, primary and secondary processes from generation through maturation and potential biodegradation, often alter the primary geochemical signature (e.g., destruction of hydrocarbon compound classes) of oil and source rocks. For example, it is known that secondary effects, such as thermal maturation and biodegradation, can impact the trace metal concentrations within hydrocarbons, and, thus, compromise the estimates made from metal concentration ratios found in samples. As such, interpretations driven by molecular data from molecular signatures impacted by maturation and secondary processes need to be vetted with a level of uncertainty that is often difficult to capture.

Therefore, it would be desirable to have a geochemical tool that utilizes a geochemical signature that retains its primary signature in oils and that can be linked back to its source, regardless of the level of maturity, biodegradation, or mixing that the oil has undergone.

Additional background references may include: Casey et al., "Analysis of Low Abundance Trace Metals and $^{51}V/^{50}V$ Isotope Ratios in Crude Oils: New Methods for Characterization and Exploration", Goldschmidt Abstracts (2015); Ventura et al., "The Stable Isotope Composition of Vanadium, Nickel, and Molybdenum in Crude Oils", Applied Geochemistry, Vol. 59, pp. 104-117 (2015); Ratié et al., "Nickel Isotope Fractionation During Laterite Ni Ore Smelting and Refining: Implications for Tracing the Sources of Ni in Smelter-Affected Soils", Applied Geochemistry, Vol. 64, pp. 136-145 (2016); Irregeher et al. "Application of Non-traditional Stable Isotopes in Analytical Ecogeochemistry Assessed by MC ICP-MS—A Critical Review", Anal. Bioanal. Chem., Vol. 408, pp. 369-385 (2016); Wu et al., "Vanadium Isotope Measurement by MC-ICP-MS", Chemical Geology, Vol. 421, pp. 17-25 (2016).

SUMMARY

Described herein are methods and techniques for utilizing a multiple metal isotope signature as an internal tracers for hydrocarbon source, alteration, and mixing. The multiple metal isotope signature may comprise a ratio of a at least two isotopes of a first metal, a ratio of at least two isotopes of a second metal, and a ratio of at least two isotopes of a third metal from a sample. The isotope ratios of the first, second, and third metal may be integrated to form the multiple metal isotope signature.

The multiple metal isotope signature may be used to provide information relating to source presence, source maturation, the origin of the hydrocarbons, oil generation, migration pathways, timing, alteration, biodegradation, mixing, maturation, source-oil correlation, environment of deposition, oil-oil correlation, source-seep correlation, hydrocarbon-seep correlation, oil-slick characterization and origin correlation, reservoir compartmentalization, mixed fluid streams, and global or regional basinal signatures.

BRIEF DESCRIPTION OF THE DRAWINGS

Advantages of the present methodologies and techniques may become apparent upon reviewing the following detailed description and accompanying drawings.

DETAILED DESCRIPTION OF THE DISCLOSURE

Figure 1:
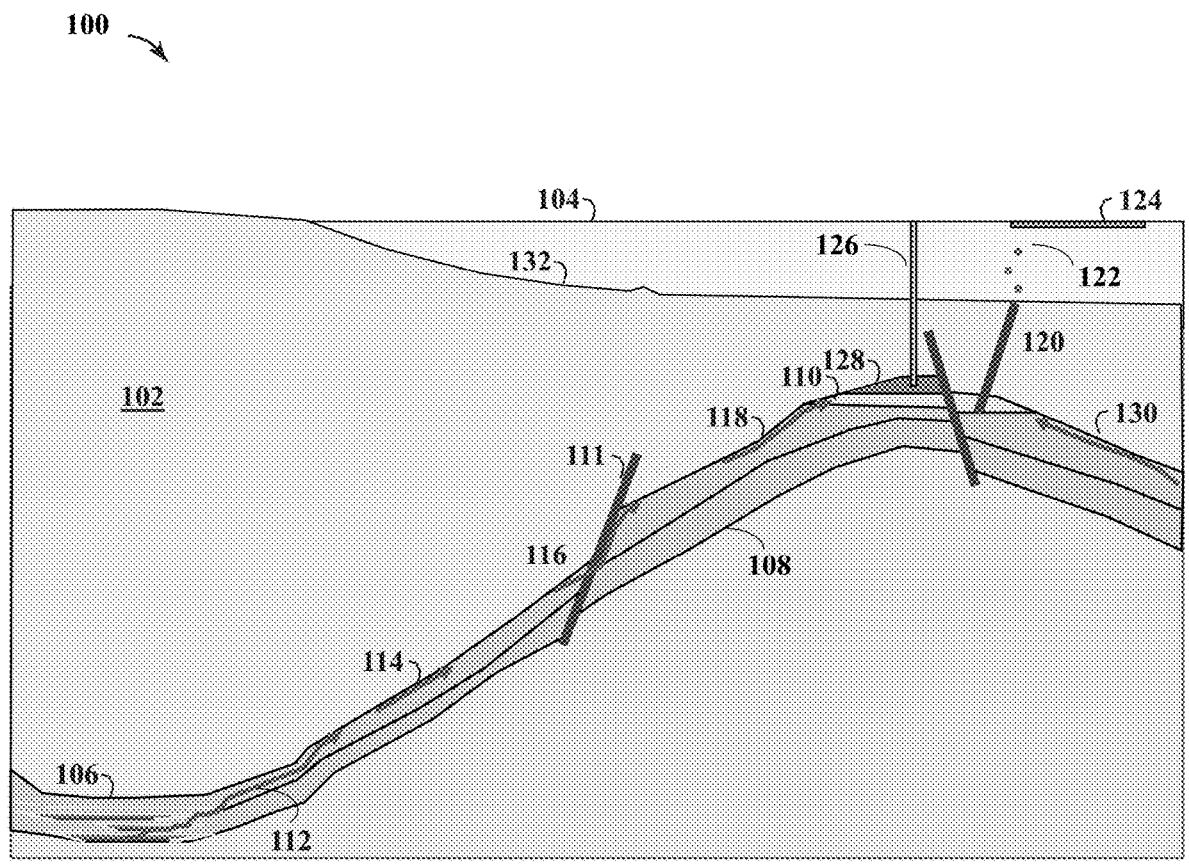
FIG. 1 is a cross-sectional view of components of a hydrocarbon system in a subsurface region.

To the extent the following description is specific to a particular embodiment or a particular use, this is intended to be illustrative only and is not to be construed as limiting the scope of the invention. On the contrary, it is intended to cover all alternatives, modifications, and equivalents that may be included within the spirit and scope of the invention.

Example methods described herein may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement various embodiments of an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

Various terms as used herein are defined below. To the extent a term used in a claim is not defined below, it should be given the broadest possible definition persons in the pertinent art have given that term as reflected in at least one printed publication or issued patent.

The term "de-risk" refers to an assessment of the possibility that undesirable species, such as $H_2S$ or $CO_2$, are present at concentrations that make hydrocarbon production or refining of hydrocarbons more difficult or reduce the value of produced hydrocarbons.

"Formation water" refers to any water that resides within the subsurface that may be present in a reservoir rock, including water in the porous media within the accumulation or immediately below, that is in contact with the hydrocarbon accumulation (e.g., the water leg). Formation water may be derived from meteoric origin; recharge of surface waters, such as rain water or seawater, that migrates through permeable rock within the subsurface; and/or water trapped in the sediment during burial that remains in place.

The term "field sample" refers to a sample containing material from the natural environment. Field samples include, but are not limited to, samples taken from any soil (encompassing all soil types and depths), water or liquid (encompassing freshwater aquatic or marine habitats), sediment (encompassing marine sediment, lake or river sediment, or mud sediment), or atmospheric dust or particulates. In some embodiments, a field sample may include drilling fluids obtained from a wellbore or hydrocarbon fluids obtained from a wellbore. In some embodiments, a field sample may be taken from the sediment or water column near a hydrocarbon seep. In such a context, the term "near" means the sample is obtained within a radius of 150 meters, or 125 meters, or 100 meters, or 75 meters, or 50 meters, or 25 meters, or 20 meters, or 15 meters, or 10 meters, or 5 meters, or 3 meters, or 1 meter from the center of the location where the seep is emanating from the surface. Reference samples may also be field samples taken from the hydrocarbon source, such as those taken away from the sediment or water column away near the hydrocarbon seep. In such a context, the term "away" means the reference sample is obtained at least 200 meters, or at least 250 meters, or at least 300 meters, or at least 350 meters, or at least 400 meters, or at least 450 meters, or at least 500 meters away from the center of the location where the seep is emanating from the surface, and in some embodiments, less than 2000 meters, or less than 1750 meters, or less than 1500 meters, or less than 1250 meters, or less than 1000 meters away from the location where the seep is emanating from the surface.

A "geologic model" is a computer-based representation of a subsurface earth volume, such as a petroleum reservoir or a depositional basin. Geologic models may take on many different forms. Depending on the context, descriptive or static geologic models built for petroleum applications can be in the form of a 2-D or 3-D array of cells, to which geologic and/or geophysical properties such as lithology, porosity, acoustic impedance, permeability, or water saturation are assigned (such properties are referred to collectively herein as "reservoir properties"). Many geologic models are constrained by stratigraphic or structural surfaces (for example, flooding surfaces, sequence interfaces, fluid contacts, and/or faults) and boundaries (for example, facies changes). These surfaces and boundaries define regions within the model that possibly have different reservoir properties.

"Hydrocarbons" are generally defined as molecules formed primarily of hydrogen and carbon atoms, such as oil and natural gas. Hydrocarbons may also include trace amounts of other elements or compounds, such as halogens, metallic elements, nitrogen, oxygen, sulfur, hydrogen sulfide ($H_2S$), and carbon dioxide ($CO_2$). Hydrocarbons may be produced from hydrocarbon reservoirs through wells penetrating a hydrocarbon containing formation or may be collected from seeps in marine and/or terrestrial environments. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicates, carbonates, diatoms, and other porous media.

As used herein, "hydrocarbon exploration" refers to any activity associated with determining the location of hydrocarbons in subsurface regions. Hydrocarbon exploration normally refers to any activity conducted to obtain measurements through acquisition of measured data associated with the subsurface formation and the associated modeling of the data to identify potential locations of hydrocarbon accumulations. Accordingly, hydrocarbon exploration includes acquiring measurement data, modeling of the measurement data to form subsurface models, and determining the likely locations for hydrocarbon reservoirs within the subsurface. The measurement data may include seismic data, gravity data, magnetic data, electromagnetic data, and the like.

As used herein, "hydrocarbon development" refers to any activity associated with planning of extraction and/or access to hydrocarbons in subsurface regions. Hydrocarbon development normally refers to any activity conducted to plan for access to and/or for production of hydrocarbons from the subsurface formation and the associated modeling of the data to identify preferred development approaches and methods. By way of example, hydrocarbon development may include modeling of the subsurface formation and extraction planning for periods of production, determining and planning equipment to be utilized and techniques to be utilized in extracting the hydrocarbons from the subsurface formation, and the like.

As used herein, "hydrocarbon operations" refers to any activity associated with hydrocarbon exploration, hydrocarbon development, and/or hydrocarbon production.

"Hydrocarbon production" or "producing hydrocarbons" refers to any activity associated with extracting hydrocarbons from the subsurface location, such as a well or other opening. Hydrocarbon production normally refers to any activity conducted to form the wellbore along with any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing of the wellbore to promote increased flow, well servicing, well logging, and other well and wellbore treatments.

As used herein, "hydrocarbon management" or "managing hydrocarbons" includes hydrocarbon extraction, hydrocarbon production, hydrocarbon exploration, identifying potential hydrocarbon resources, identifying well locations, determining well injection and/or extraction rates, identifying reservoir connectivity, acquiring, disposing of and/or abandoning hydrocarbon resources, reviewing prior hydrocarbon management decisions, and any other hydrocarbon-related acts or activities.

As used herein, "machine-readable medium" refers to a medium that participates in directly or indirectly providing signals, instructions and/or data. A machine-readable medium may take forms, including, but not limited to, non-volatile media (e.g. ROM, disk) and volatile media (RAM). Common forms of a machine-readable medium include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, and other media from which a computer, a processor or other electronic device can read.

The term "isotope" refers to one of two or more atoms with the same atomic number but with different numbers of neutrons. For example, naturally occurring vanadium (V) can be present as one of two isotopes: $^{51}V$, which is a stable isotope that has 23 protons and 28 neutrons, and $^{50}V$, which is a radioactive isotope that has 23 protons and 27 neutrons.

The term "isotopologue" refers generally to molecules that have the same chemical composition, but have a different isotopic signature. For example, methane contains one atom of carbon and four atoms of hydrogen. Each atom in the methane structure can contain one of the two stable isotopes of that atom, and as such, there are ten possible isotopologues of methane.

The term "multiply substituted isotopologue" refers generally to an isotopologues that contains at least two rare isotopes in its structure. For example, a multiply substituted isotopologue of methane contains one $^{13}C$ atom and one deuterium (D) atom, or at least two D atoms in the absence of a $^{13}C$ atom.

The term "clumped isotopologue" refers generally to an isotopologue that contains at least two rare isotopes that share a common chemical bond in its structure. For example, a clumped isotopologue of methane contains one $^{13}C$ atom that shares a chemical bond with at least one D atom.

The term "position specific isotope signature" refers generally to a compound that has multiple chemically or structurally distinct positions for a rare isotope to reside. For example, a position specific isotope effect in propane could refer to the position of the $^{13}C$ atom, which can be positioned either at the center of the compound or one of the end positions, or the position of the D atom, which can be attached to either a central or end position carbon.

The term "signatures" refers to a relative abundance, concentration, and/or ratio of elements and/or isotopes of a given species within a sample. For example, a signature may refer to chemical or geochemical compositions, components, concentrations, or ratios of one or more elements, isotopes, compounds, or the like. The signature may be derived from one or more of the following hydrocarbons, metal isotopes, noble gases, clumped isotopes, water, non-hydrocarbon gases, or the like.

The term "stochastic distribution" refers to a system where the stable isotopes in a given population of molecules are distributed randomly among all possible isotopologues in a given species. The stochastic distribution is the reference frame from which deviations are measured and is used to provide a baseline to identify anomalies that may be associated with secondary isotope exchange processes.

The term "noble gases" refers to a series of chemically inert elements that exhibit similar properties. The six noble gases that occur naturally are helium (He), neon (Ne), argon (Ar), krypton (Kr), xenon (Xe), and radon (Ra).

The term "radiogenic" refers to generation or creation of a substance through radioactive decay of another substance. For example, $^{50}Ti$ and $^{50}Cr$ are radiogenic isotopes created by the radioactive decay of $^{50}V$.

The term "region of interest" refers to an interval, compartment, or reservoir where hydrocarbons, non-hydrocarbons gases, and/or water may reside. Regions of interest may refer to multiple intervals, compartments, or reservoirs where hydrocarbons, non-hydrocarbon gases, and/or water may reside.

The terms "inter-regional" or "inter-compartment" refers to comparisons of multiple geochemical fingerprints derived from multiple regions of interest including, but not limited to, compartments, intervals, or reservoirs. Deviations in "inter-regional" fingerprints may be derived from different proportions of individual regions of interest contributing to a combined flow stream during production, multiple compartments that are connected in the subsurface that produce a fingerprint consistent with multiple inputs, and the like.

The terms "intra-regional" or "intra-compartment" refer to comparisons of multiple geochemical fingerprints derived from one region of interest including, but not limited to, compartments, intervals, or reservoirs. Deviations in "intra-regional" fingerprints may be derived from changes in the properties of one region of interest.

The term "fingerprint" or "geochemical fingerprint" refers to a collection of geochemical signatures that are associated with a particular region of interest.

The term "residence time" refers to the time period that formation water and/or a chemical species has been present within the subsurface and can be considered the age of the formation water and/or chemical species. For example, the residence time may refer to the time period that a chemical species, such as a dissolved anion or cation, has been present within the subsurface.

As used herein, the term "signatures" refers to the relative abundances, concentrations, and/or ratios of various elements and isotopes of a given species.

The term "thermogenic" refers to hydrocarbons generated from kerogen that is currently or has in the past been subjected to high temperatures and pressures.

Described herein are methods and techniques for utilizing multicomponent metal isotope signatures in hydrocarbon systems for hydrocarbon exploration, production, and development processes. In particular, the processes described herein utilize a geochemical tool that integrates multiple metal isotope signatures in bulk and compound specific ratios. The utilization of both bulk concentrations and compound specific metal isotope ratios allows for the preservation of a primary hydrocarbon signature even after alteration, thus allowing for determination of source rock environment of deposition, source rock to oil correlation, oil to oil correlation, oil maturity, oil migration, biodegradation, reservoir connectivity, and downstream mixture tracing. Further, the use of the multicomponent metal isotope signatures may allow for more effective reservoir surveillance and for more effective monitoring of hydrocarbon production operations. For example, the use of the multicomponent metal isotope signatures may allow for improved sensitivity in distinguishing between hydrocarbon flows from different regions of interest. As another example, the use of the multicomponent metal isotope signatures may provide for the ability to distinguish between hydrocarbon fluid sources in hydrocarbon refining operations.

FIG. 1 is a cross sectional diagram 100 of components of a hydrocarbon system in a subsurface region. In diagram 100, components and events in a hydrocarbon system are provided for a subsurface region 102, which may be at least partially below a body of water 104. The processes of a hydrocarbon system involve generation, migration, trap formation, accumulation or leakage to a seep, and/or preservation. The elements (or components) of the hydrocarbon system include various portions of a formation, such as source rocks 106, reservoir rocks 108, and seal rocks 128. Hydrocarbon systems analysis may involve determining source presence, source maturation, trap presence, migration pathways, reservoir presence, trap seal presence, and timing. The hydrocarbons may be produced through a wellbore 126.

As an example, the hydrocarbon system process may involve various steps to form current hydrocarbon locations. First, hydrocarbons are generated, which occurs in source rock 106. Then, the hydrocarbons migrate from the source rock 106 through faults and fractures, such as fracture 111, as shown by arrows 112, 114, 116, and 118. Hydrocarbons accumulate in a reservoir 110. Accumulation of hydrocarbons can only occur if a trapping structure is present at the same time or before hydrocarbons migrate through the reservoir rock 108 if an adequate seal rock 128 is in place. Hydrocarbons can be stored in an accumulation 110 and preserved, as shown by seal rocks 128 or may be altered by a fracture through a fault line 120. If limited by subsurface geology, the hydrocarbons may be trapped in hydrocarbon accumulations 110, such as a gas reservoir and/or an oil/gas reservoir. Hydrocarbons may bubble and seep 122 from the subsea surface 132 into the body of water 104, via a fault 120, and form an oil slick 124 on the surface of the body of water 104.

Described herein are methods and techniques for evaluating primary geochemical signatures that can be used as robust internal tracers for hydrocarbon source, alteration, and mixing. That is, the geochemical signatures described herein are resilient to changes that occur during hydrocarbon generation, migration, and other secondary effects (such as from thermal maturation and biodegradation). As such, the geochemical signatures described herein can be used to provide information relating to source presence, source maturation, the origin of the hydrocarbons, oil generation, migration pathways, timing, alteration, biodegradation, mixing, maturation, source-oil correlation, environment of deposition, oil-oil correlation, source-seep correlation, hydrocarbon-seep correlation, oil-slick characterization and origin correlation, reservoir compartmentalization, mixed fluid streams, and global or regional basinal signatures. Further, the geochemical signatures described herein can be linked back to the hydrocarbon source, regardless of the level of maturity, alteration, biodegradation, or mixing that the hydrocarbon has undergone. That is, the use of the multicomponent metal isotope signatures described herein can be used across both upstream and downstream applications.

As described above the common approach to the use of metal isotopes in hydrocarbon studies is to measure a single metal isotope (e.g., V or Ni only) in combination with the bulk ratios of the metal concentrations of interest (e.g., V/(V+Ni)). However, secondary effects, such as alteration of the hydrocarbons can impact the metal concentrations and thus compromise the metal concentration ratios. As such, the conventional approach may produce inaccurate results.

In contrast to the conventional approach to the use of metal isotopes in hydrocarbon studies, the present invention provides an improved geochemical tool that utilizes and integrates multiple metal isotope measurements and utilizes compound specific ratios. In particular, the geochemical tool may comprise measurement of both bulk concentrations and compound specific metal isotope ratios. As such, the geochemical tool described herein is able to measure a primary signature that is preserved even during hydrocarbon alteration, which can then be used to determine source rock environment of deposition, source rock to oil correlation, oil to oil correlation, oil maturity, oil migration, biodegradation, reservoir connectivity, as well as other downstream applications such as linking oils to a source feed and deconvuluting mixtures to determine source.

Figure 2:
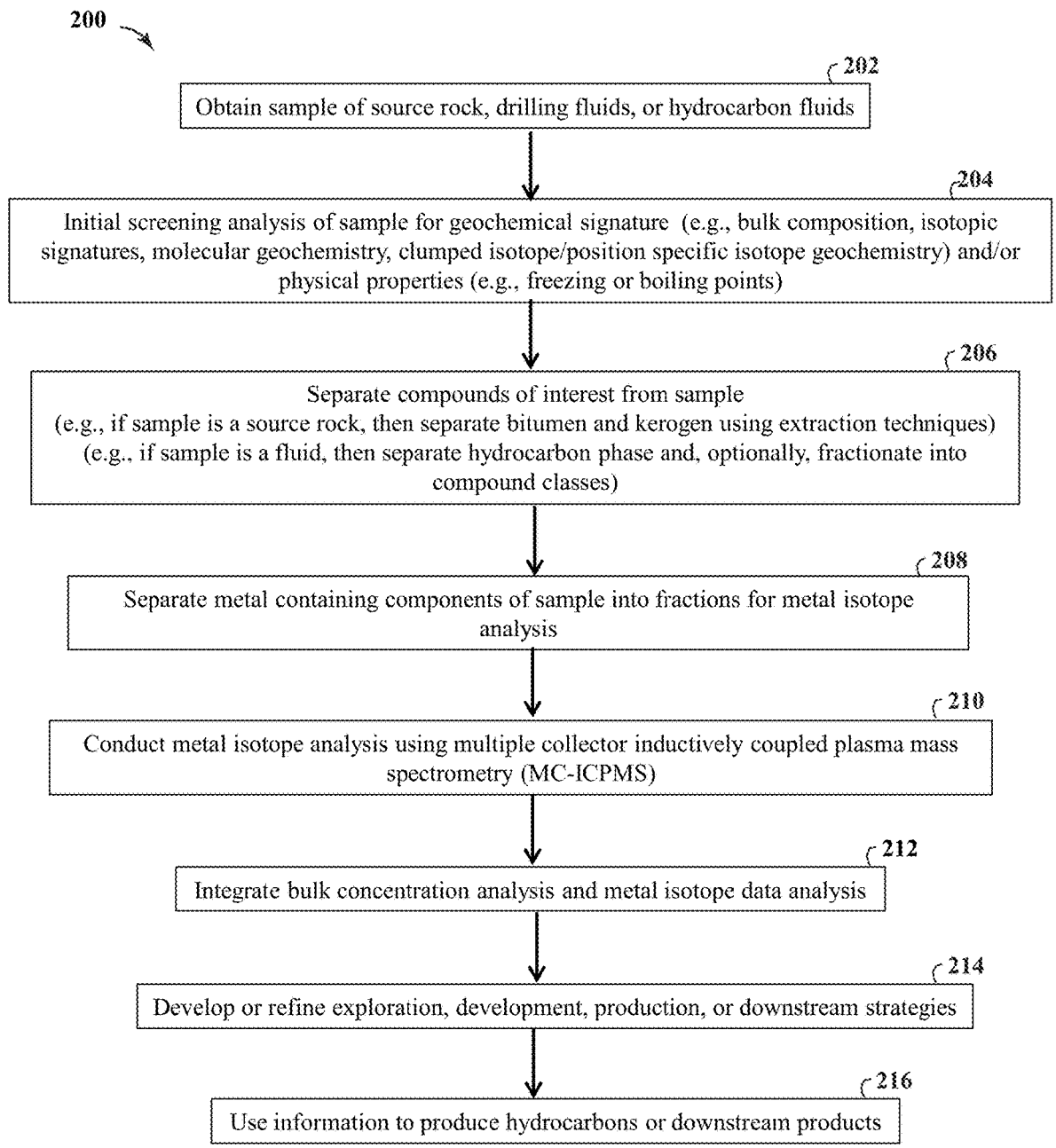
FIG. 2 is a flow diagram of an exemplary method utilizing metal isotopes in accordance with the disclosed methodologies and techniques.

FIG. 2 is a flow diagram 200 of an exemplary method in accordance with embodiments of the present techniques. The flow diagram 200 includes the acquisition of a sample, analysis of the sample, measurement of metal isotopes and bulk metal concentrations, integrating the bulk concentration and metal isotope data, and utilizing the information to develop or refine exploration, development, production, or downstream strategies.

At block 202 a sample of hydrocarbon(s) is obtained. The sample may be from a source rock, from drilling fluids, or from hydrocarbon fluids. The sample can be in the form of oil and/or gas obtained from the subsurface, at a surface location, such as seep, and may be in the form of free oil and/or gas, as solid hydrocarbons, or may be trapped within a rock sample. As another example, in downstream refining applications, the sample may taken from the inlet or outlet of a distillation tower, such as an asphaltene distillation tower or a vacuum distillation tower, or from a hydrotreater or hydrocracker, or from any other process equipment in the refinery.

At block 204 an initial screening analysis may be performed to determine a geochemical signature or physical properties of the sample. For example, determining a geochemical signature may comprise analyzing the sample to determine a bulk composition, non-metal isotopic signatures, molecular geochemistry, measurement of the hydrocarbon clumped isotopes or position specific isotope geochemistry. For example, determining physical properties of the sample may comprise analysis to determine freezing and/or boiling points of the sample.

As an example, the sample may be analyzed to determine a clumped isotope signature or position specific isotope signature of the different hydrocarbons (e.g., methane, propane, butane, etc.) within the sample. If methane is utilized, an analysis can be undertaken to measure the clumped doubly substituted isotopologue $^{13}CH_3D$ and the doubly substituted isotopologues $^{12}CH_2D_2$. The measurement of such isotopologues can be conducted using multiple techniques, such as mass spectrometry and/or laser-based spectroscopy. The methane clumped isotope signature (e.g., the $^{13}CH_3D$ isotopologue signature) can then be used to determine information about the temperature at which the methane was generated, as the methane clumped isotope signature is known to be preserved even as the methane is exposed to different temperatures during migration or uplift of the sediments in which the methane is constrained. See e.g., Stolper et al. "Formation Temperatures of Thermogenic and Biogenic Methane", *Science*, Vol. 344, pp. 1500-1503 (2014). In contrast, measurement of the clumped isotope signatures of other hydrocarbon molecule species may provide information on different parts of the sample's history due to the hydrocarbon species different kinetic behaviors. For example, analysis of the decane clumped isotope signature may provide information on a historical temperature that reflects the temperature at which the sample has been stored over the past several years, as the decane molecules may undergo intro-molecular isotope exchange over faster timescales than methane.

As another example, gas chromatography and mass spectrometry analysis may be performed (such as, GC/MS, GC/GC/MS, or liquid chromatography) to determine a bulk composition signature of the sample. For example, measurement of the abundance of noble gas isotopes can be conducted following standard extracting techniques using mass spectrometry.

As a further example, various techniques, such as XRD, may be used to provide information about the mineralogy of the reservoir from which the sample was obtained.

At block 206, the compounds of interest may be separated from the sample. For example, if the sample is a source rock, then the bitumen and kerogen can be separated via known extraction techniques from the rock. As another example, if the sample is a fluid, then the hydrocarbon phase of the fluid can be separated from other fluids in the sample (e.g., drilling fluids, formation waters, etc.). Optionally, once the hydrocarbon phase of the fluid sample is separated the hydrocarbon phase can be fractionated into different compound classes.

At block 208, the metal containing components of the sample are separated from the sample, and the metal containing components are separated into fractions for metal isotope analysis.

At block 210, metal isotope analysis is conducted. The metal isotope ratios described herein can be measured by any process known in the art. However, in preferred embodiments, the metal isotope ratios are measured using multiple collector inductively coupled plasmas mass spectrometry (MC-ICPMS), fourier transform ion cyclotron resonance mass spectrometry (FTICR-MS) combined with chemical separation procedures and quantitative purification of extracts and hydrocarbons. These techniques allow for highly precise and accurate isotope measurements, such as the measurement of vanadium isotopes ($\delta^{51}$ V), nickel isotopes ($\delta^{60}$ Ni, $\delta^{60/58}$ Ni), molybdenum ($\delta^{98}$Mo, $\delta^{98/95}$ Mo), as well as measurement of chromium, iron, cobalt, zinc, and copper isotopes, as well as measurement of any of the isotopes described in Table 1.

TABLE 1

Exemplary Metal Isotopes of Interest

| Isotope | Approximate Naturally Occurring Amount (%) | # of Protons | # of Neutrons | Radiogenic Daughters |
|---|---|---|---|---|
| $^{50}$Cr | 4.3% | 24 | 26 | $^{50}$Ti (1.8 × 10$^{17}$ years ½ life) |
| $^{52}$Cr | 83.8% | 24 | 28 | Stable |
| $^{53}$Cr | 9.5% | 24 | 29 | Stable |
| $^{54}$Cr | 2.4% | 24 | 30 | Stable |
| $^{63}$Cu | 69.2% | 29 | 34 | Stable |
| $^{65}$Cu | 30.8% | 29 | 36 | Stable |
| $^{54}$Fe | 5.8% | 26 | 28 | Observationally Stable (½ life of 3.1 × 10$^{22}$ years) |
| $^{56}$Fe | 91.8% | 26 | 30 | Stable |
| $^{57}$Fe | 2.1% | 26 | 31 | Stable |
| $^{58}$Fe | 0.3% | 26 | 32 | Stable |
| $^{92}$Mo | 14.6% | 42 | 50 | Stable |
| $^{94}$Mo | 9.2% | 42 | 52 | Stable |
| $^{95}$Mo | 15.9% | 42 | 53 | Stable |
| $^{96}$Mo | 16.7% | 42 | 54 | Stable |
| $^{97}$Mo | 9.6% | 42 | 55 | Stable |
| $^{98}$Mo | 24.3% | 42 | 56 | Stable |
| $^{100}$Mo | 9.7% | 42 | 58 | $^{100}$Ru (8.5 × 10$^{18}$ years ½ life) |

TABLE 1-continued

Exemplary Metal Isotopes of Interest

| Isotope | Approximate Naturally Occurring Amount (%) | # of Protons | # of Neutrons | Radiogenic Daughters |
|---|---|---|---|---|
| $^{58}$Ni | 68.1% | 28 | 30 | Observationally Stable |
| $^{60}$Ni | 26.2% | 28 | 32 | Stable |
| $^{61}$Ni | 1.1% | 28 | 33 | Stable |
| $^{62}$Ni | 3.6% | 28 | 34 | Stable |
| $^{64}$Ni | 0.9% | 28 | 36 | Stable |
| $^{96}$Ru | 5.5% | 44 | 52 | Observationally Stable |
| $^{98}$Ru | 1.9% | 44 | 54 | Stable |
| $^{99}$Ru | 12.8% | 44 | 55 | Stable |
| $^{100}$Ru | 12.6% | 44 | 56 | Stable |
| $^{101}$Ru | 17.1% | 44 | 57 | Stable |
| $^{102}$Ru | 31.6% | 44 | 58 | Stable |
| $^{104}$Ru | 18.6% | 44 | 60 | Observationally Stable |
| $^{46}$Ti | 8.3% | 22 | 24 | Stable |
| $^{47}$Ti | 7.4% | 22 | 25 | Stable |
| $^{48}$Ti | 73.7% | 22 | 26 | Stable |
| $^{49}$Ti | 5.4% | 22 | 27 | Stable |
| $^{50}$Ti | 5.2% | 22 | 28 | Stable |
| $^{51}$V | 99.7% | 23 | 28 | Stable |
| $^{50}$V | 0.3% | 23 | 27 | Approx. 83% $^{50}$Ti and 17% $^{50}$Cr (1.5 × 10$^{17}$ years ½ life) |
| $^{64}$Zn | 49.2% | 30 | 34 | Observationally Stable |
| $^{66}$Zn | 27.7% | 30 | 36 | Stable |
| $^{67}$Zn | 4.0% | 30 | 37 | Stable |
| $^{68}$Zn | 18.5% | 30 | 38 | Stable |
| $^{70}$Zn | 0.6% | 30 | 40 | Observationally Stable |

At block 212 the data from the bulk metal concentration analysis and the metal isotope analysis is integrated as described further with reference to FIGS. 3 and 4.

At block 214, the multicomponent metal isotope signature determined in block 212 may be used to develop or refine a hydrocarbon exploration, development or production strategy, or to develop or refine a downstream refining strategy. For example, the multicomponent metal isotope signature can be used to link sample to a source (such as a source rock), as well as to address questions pertaining to the history of the sample (such as generation, alteration, migration, mixing, and contamination). In particular the hydrocarbon exploration, development, or production strategy can be developed or refined using information from the multicomponent metal isotope signature, such as information about source presence, source maturation, migration pathways, timing of generation, alteration, biodegradation, mixing of hydrocarbons, maturation, source to oil correlations, oil to oil correlations, source to hydrocarbon seep correlation, hydrocarbon-seep fingerprinting, hydrocarbon-slick to source correlation, and/or hydrocarbon-slick fingerprinting. The information can also be used to develop or refine a downstream refining strategy, such as by identifying origin of a hydrocarbon stream, fingerprinting hydrocarbon streams, and recognition and separation of mixed hydrocarbon streams.

At block 216 the information can be used to produce hydrocarbons from subsurface accumulations or to produce downstream refining products. For example, producing hydrocarbons may include operations, such as modeling the location to drill a well, directing acquisition of data for placement of a well, drilling a well, building surface facilities to produce the hydrocarbons, along with other operations conducted in and/or associated with the well after the well is completed. Accordingly, producing hydrocarbons includes hydrocarbon extraction, along with injection of gas or liquid for increasing drive pressure, mobilizing the hydrocarbon or treating by, for example, chemicals or hydraulic fracturing the wellbore to promote increased flow, well servicing, well logging, and other well and wellbore treatments. As another example, producing downstream products may include refining the hydrocarbons to produce fuels and lubricants, or utilizing higher carbon species (e.g, ethane and propane) to produce downstream chemical products such as polyethylene or polypropylene.

Figure 3A:
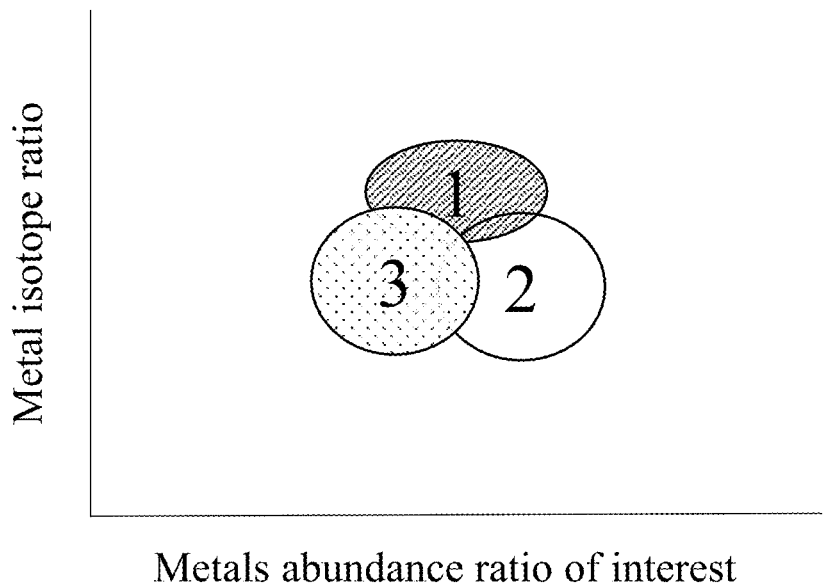
FIGS. 3A and 3B illustrate the use of multi-metal isotope measurements to determine sample specific information.
Figure 3B:
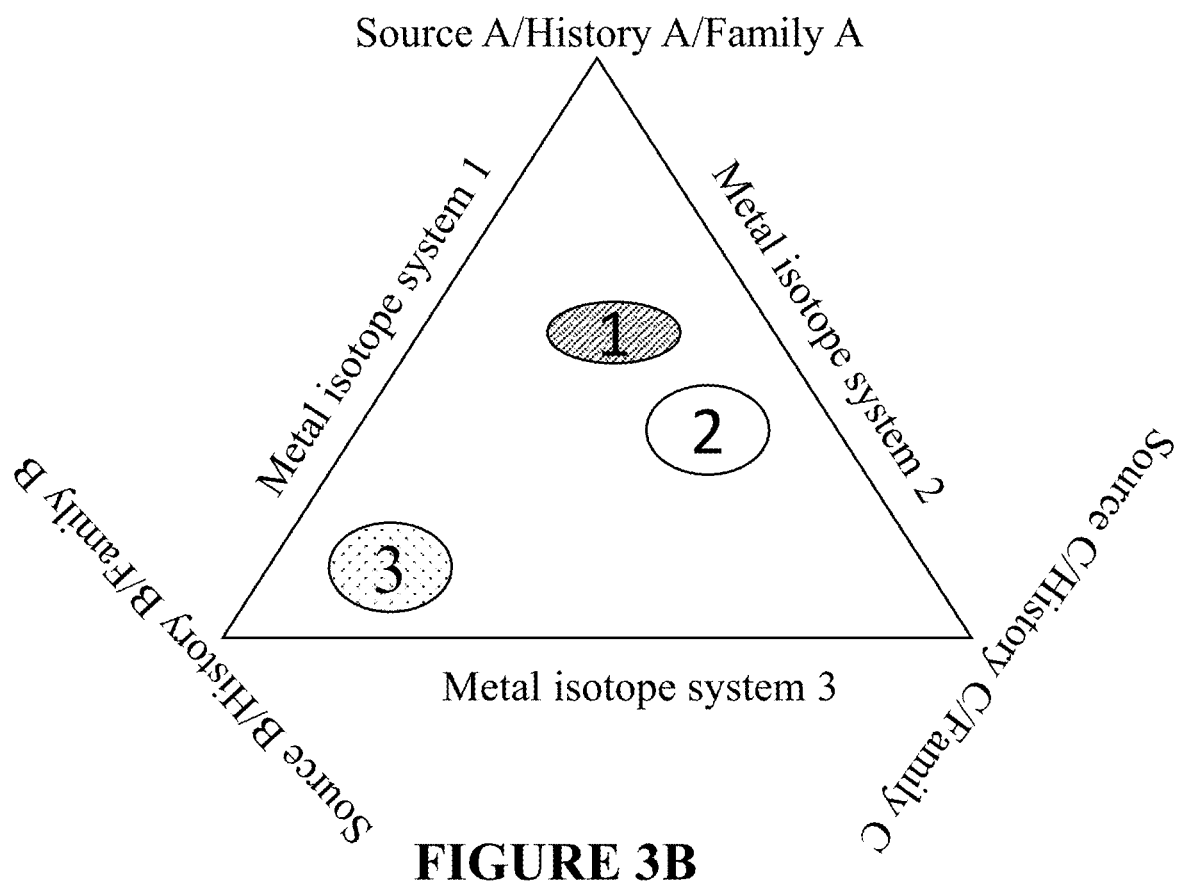

FIG. 3 illustrates a comparison of a conventional analysis in FIG. 3A and the multi-metal isotope measurements of the present techniques in FIG. 3B. FIG. 3A illustrates a comparison of a single metal isotope ratio (e.g., $\delta^{51}$V or $\delta^{60}$Ni) to the metal abundance ratio of interest (e.g., V/(V+Ni)) for three sample oils (Sample 1, Sample 2, and Sample 3). As seen in FIG. 3A the signatures that result overlap and it would be difficult to differentiate the samples from one another or to deconvolute a mixture of the samples. However, as illustrated in FIG. 3B when multi-metal isotope measurements are compared for each of the three samples, increased resolution and sample characterization results. For example, in FIG. 3B a plot of the vanadium metal isotope system can be plotted against the nickel and molybdenum isotope systems. The integration of the multi-metal isotope measurements allows for separation of the samples. This can allow for more specific identification of the samples based on sample origin (e.g., source), history (including formation, maturation, alteration, migration, and contamination), hydrocarbon family, etc. Thus, as illustrated in FIG. 3B utilizing multiple metal isotope ratios (e.g., such as vanadium, nickel, and molybdenum) as compared to a single metal isotope ratio in FIG. 3A, can provide more detailed characterization of the samples.

In some embodiments, the present methodologies may comprise a comparison of ratios of multiple metal isotopes within multiple samples to determine if the samples are from the same source and/or have the same history. For example, the methodology may comprise analyzing a sample to determine the concentration of at least two isotopes of at least three different metals. An isotope ratio of the first metal of interest, a second metal of interest, and a third metal of interest may then be integrated to provide a multiple metal isotope signature of the sample. The multiple metal isotope signature of a first sample may then be compared to a multiple metal isotope signature of another sample or to a database of multiple metal isotope signatures to aid in determining the origin of the first sample.

In some embodiments, the process may comprise analyzing a sample to determine the concentrations of at least two isotopes of vanadium, at least two isotopes of nickel, and at least two isotopes of molybdenum within the sample. The isotope concentrations may then be used to formulate an isotope ratio for each metal of interest (i.e., for vanadium, nickel, and molybdenum). For example, an isotope ratio ($\delta^{51}V$) of $^{51}V$ to $^{50}V$ (i.e., $^{51}V/^{50}V$) may be determined for vanadium. For example, an isotope ratio ($\delta^{60}Ni$) of $^{60}Ni$ to $^{58}Ni$ (i.e., $^{60}Ni/^{58}Ni$), or $^{60}Ni$ to $^{61}Ni$, or $^{60}Ni$ to $^{62}Ni$, $^{60}Ni$ to $^{64}Ni$, may be determined for nickel. For example an isotope ratio of $^{100}Mo$ to $^{92}Mo$, or $^{100}Mo$ to $^{94}Mo$, or $^{100}Mo$ to $^{95}Mo$, or $^{100}Mo$ to $^{96}Mo$, or $^{100}Mo$ to $^{97}Mo$, or $^{100}Mo$ to $^{98}Mo$, may be determined for molybdenum. Alternatively, an isotope ratio ($\delta^{98}Mo$) of $^{98}Mo$ to $^{96}Mo$ (i.e., $^{98}Mo/^{95}Mo$), or $^{98}Mo$ to $^{92}Mo$, or $^{98}Mo$ to $^{94}Mo$, or $^{98}Mo$ to $^{96}Mo$, or $^{98}Mo$ to $^{97}Mo$, or $^{98}Mo$ to $^{100}Mo$, may be determined for molybdenum. In some embodiments, the isotope ratio for a metal of interest may comprise a ratio of three or more isotopes. For example, a ratio of $^{58}Ni$ to $^{60}Ni$ to $^{62}Ni$ may be determined. While ratios of vanadium, nickel, and molybdenum may be preferred, other metals of interest may include chromium, iron, cobalt, zinc, and copper, among others. Further, in some embodiments, the multiple metal isotope signature may comprise ratios of four or more metals of interest, or five or more metals of interest, or six or more metals of interest, where isotope ratios for at least two isotopes of each metal of interest are used to determine a multiple metal isotope signature of the sample.

The isotope ratios of the metals of interest may then be integrated together to form the multiple metal isotope signature. For example, a ternary plot may be created with each axis plotting the isotope ratio for a different metal of interest. In embodiments where four metals of interest a quaternary plot may be used.

As illustrated in FIG. 4, utilizing compound-specific metal isotope ratios can provide additional resolution and characterization of the samples.

Figure 4A:
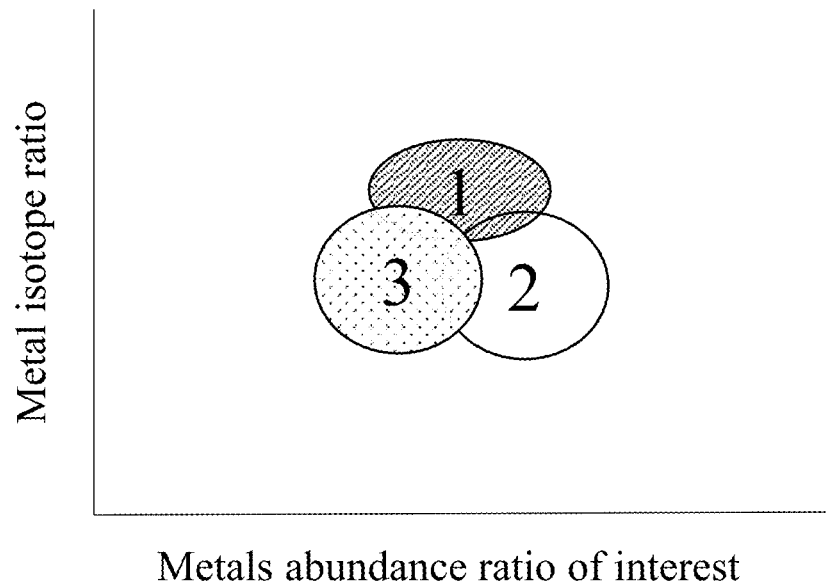
FIGS. 4A and 4B illustrate the use of compound-specific metal isotope ratios to determine sample specific information.
Figure 4B:
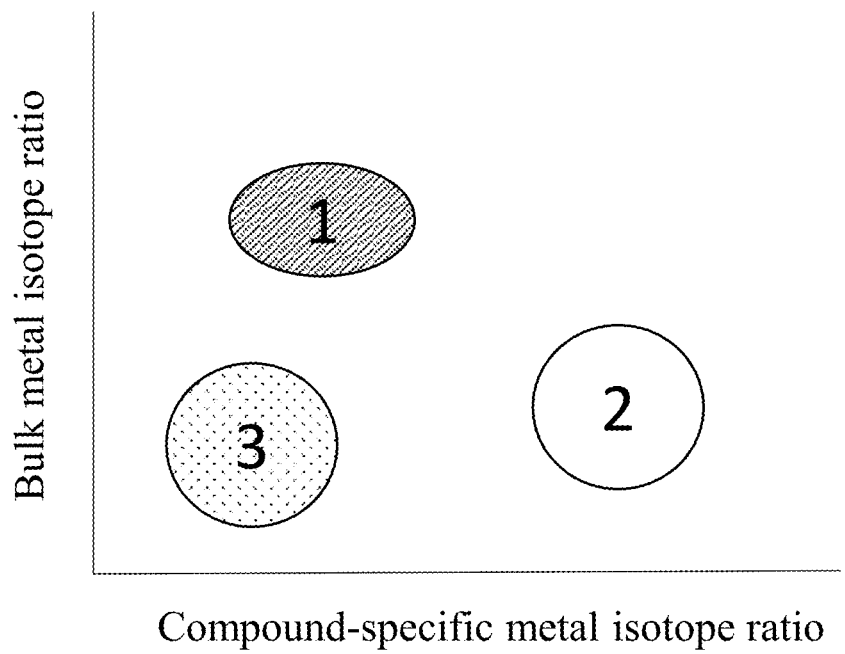

FIG. 4 illustrates a comparison of a conventional analysis in FIG. 4A and the multicomponent metal isotope measurements of the present techniques in FIG. 4B. FIG. 4A illustrates a comparison of a single metal isotope ratio (e.g., V or Nickel) to the metal abundance ratio of interest (e.g., V/(V+Ni)) for three sample oils (Sample 1, Sample 2, and Sample 3). As seen in FIG. 4A the signatures that result overlap and it would be difficult to differentiate the samples from one another or to deconvolute a mixture of the samples. However, as illustrated in FIG. 4B when compound-specific metal isotope measurements are compared for each of the three samples, increased resolution and sample characterization results. For example, in FIG. 4B a plot of the vanadium metal isotope ratio can be plotted against the a compound specific isotope ratio of molybdenum or nickel.

The multiple metal isotope signatures described above can be integrated with other geochemical techniques such as biomarker signatures, stable isotopes of carbon and hydrogen signatures, clumped isotope signatures, noble gas signatures, non-hydrocarbon gas composition signatures (e.g., $H_2S$, $N_2$, and/or $CO_2$). The integrated signatures can be used to fingerprint the sample and provide information about the source facies, thermal maturity, thermogenic vs. biogenic origin of the sample, origin of non-hydrocarbon gases etc. The fingerprint for the sample is unique to the individual region of interest (e.g., compartments, intervals, or reservoirs of interest). Once region of interest fingerprints are obtained they can be used in wide range of reservoir surveillance operations, hydrocarbon production strategies to enhance depletion strategies, and in downstream operations to trace and identify sources as they move through a petroleum refinery.

For example, produced fluids may be analyzed for the multiple metal isotope signature and other geochemical signatures to develop a fingerprint for the sample. As production continues, changes in the signatures can be monitored to provide information about changes in source of the produce fluids, identify issues with the production of the wellbore (e.g., breakthrough from different compartments within the reservoir). Such reservoir surveillance operations may further include monitoring production allocation, reservoir connectivity, water breakthrough, etc.

Similar to reservoir surveillance, in refining operations, the feedstock entering the refinery can be monitored to identify changes in source of the hydrocarbons. For example, when hydrocarbons from multiple sources are blended together in the refinery, it would be desirable to retain the ability to link the hydrocarbons in the blend back to the source so that appropriate steps may be taken in the refinery to mitigate fouling caused by the use of disparate sources.

Figure 5:
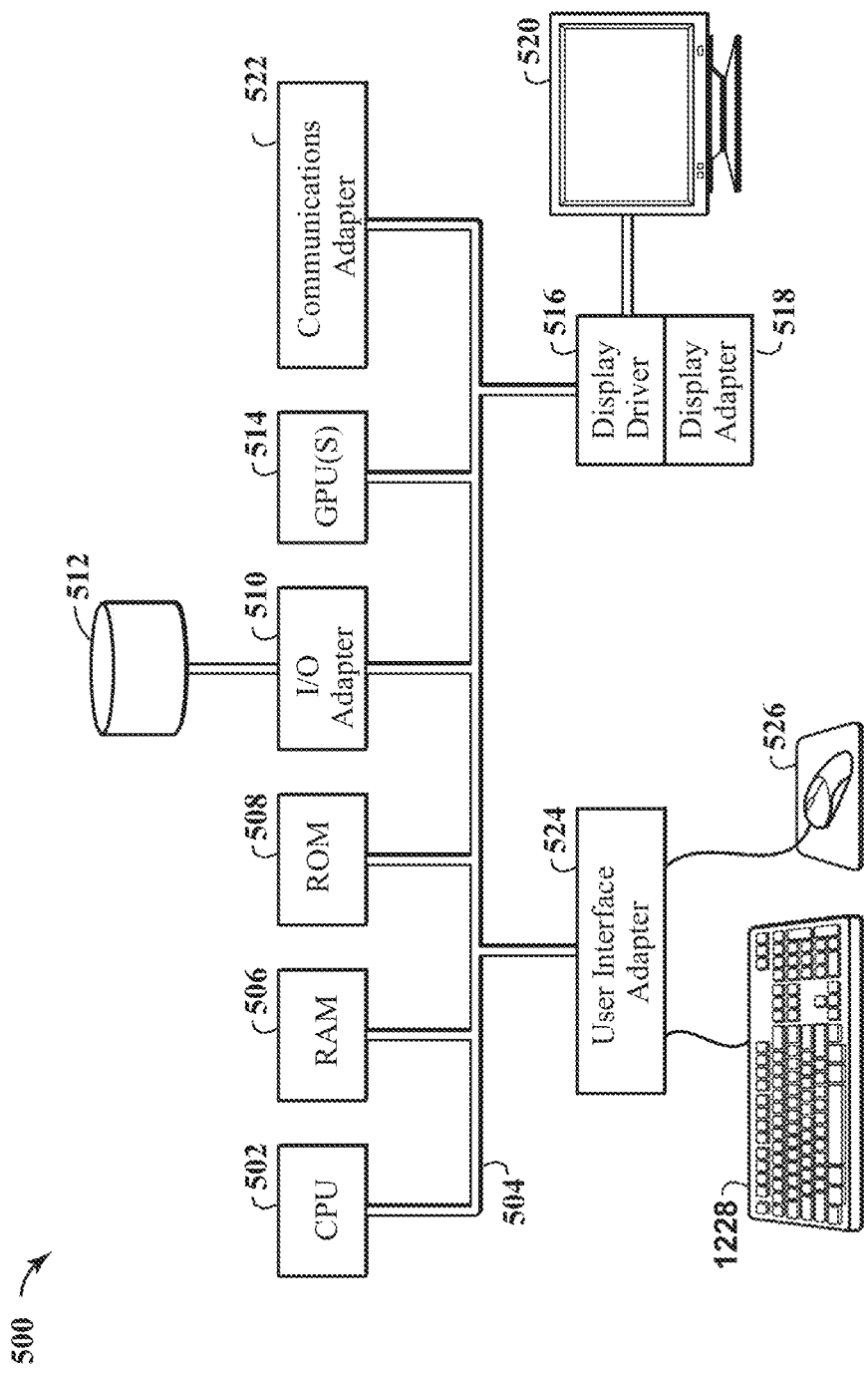
FIG. 5 is a diagram of an exemplary computing system that may be used with the present methodologies and techniques.

FIG. 5 is a block diagram of a computer system 500 which may be used with exemplary embodiments of the present methods. A central processing unit (CPU) 502 is coupled to a system bus 504. The CPU 502 may be any general-purpose CPU, although other types of architectures of CPU 502 (or other components of system 500) may be used as long as CPU 502 (and other components of system 500) support the inventive operations as described herein. The CPU 502 may execute the various logical instructions according to the various exemplary embodiments described herein. For example, the CPU 502 may execute machine-level instructions for processing according to the operation flow diagram illustrated in FIG. 2.

The computer system 500 may also include computer components such as a random access memory (RAM) 506, which may be SRAM, DRAM, SDRAM, or the like. The computer system 500 may also include read-only memory (ROM) 508, which may be PROM, EPROM, EEPROM, or the like. RAM 506 and ROM 508 hold user and system data and programs, as is known in the art. The computer system 500 may also include an input/output (I/O) adapter 510, a communications adaptor 522, a user interface adaptor 524, and a display adaptor 518. The I/O adaptor 510, the user interface adaptor 524, and/or communications adaptor 522 may, in certain embodiments, enable a user to interact with computer system 500 in order to input information.

The I/O adaptor 510 preferably connects a storage device(s) 512, such as one or more of hard drive, compact disc (CD) drive, floppy disk drive, tape drive, etc. to computer system 500. The storage device(s) 512 may be used when RAM 506 is insufficient for the memory requirements associated with storing data for operations of embodiments of the present methods and techniques. The data storage of the computer system 500 may be used for string information and/or other data used or generated as disclosed herein. The communications adaptor 522 may couple the computer system 500 to a network (not shown), which may enable information to be input to and/or output from system 500 via the network (for example, the Internet or other wide-area network, a local-area network, a public or private switched telephony network, a wireless network, and any combination of the foregoing). User interface adaptor 524 couples user input devices, such as keyboard 1228, a pointing device 526, and the like to computer system 500. The display adaptor 518 is driven by the CPU 502 to control, through a display driver 516, the display on a display device 520. Information and/or representations pertaining to a portion of a supply chain design or a shipping simulation, such as displaying data corresponding to a physical or financial property of interest, may thereby be displayed, according to certain exemplary embodiments.

The architecture of system 500 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to embodiments.

As an example, machine-readable logic or code may be used or executed with a computing system, such as computing system 500. The computer system may be used for exploration, production, and development of hydrocarbons. The computer system may include a processor, memory stored in communication with the processor, and a set of instructions stored in memory and accessible by the processor. The set of instructions, when executed by the processor, are configured to: obtain information associated with a hydrocarbon sample; conduct an initial screening analysis of the sample for geochemical signatures comprising one or more of bulk composition, isotopic signatures, molecular geochemistry, clumped isotope/position specific isotope geochemistry, and physical properties (e.g., freezing or boiling points) of the hydrocarbon sample; separate compounds of interest from the sample; separate metal containing components of the sample into fractions for metal isotope analysis; conduct metal isotope analysis on the sample; integrate bulk metal concentration analysis and metal isotope data analysis; and/or develop or refine hydrocarbon exploration, development, production strategies.

It should be understood that that preceding is merely a detailed description of specific embodiments of the invention and that numerous changes, modifications, and alternatives to the disclosed embodiments can be made in accordance with the disclosure herein without departing from the scope of the invention. The preceding description therefore, is not meant to limit the scope of the invention. Rather, the scope of the invention is to be determined only by the appended claims and their equivalents. It is also contemplated that structures and features embodied in the present embodiments can be altered, rearranged, substituted, deleted, duplicated, combined, or added to each other.

The invention claimed is:

1. A method of producing hydrocarbons comprising:
(a) obtaining one or more samples from a well in a region of interest;
(b) analyzing the sample to determine a ratio of at least two isotopes of a first metal;
(c) analyzing the sample to determine a ratio of at least two isotopes of a second metal;
(d) analyzing the sample to determine a ratio of at least two isotopes of a third metal;
(e) integrating the isotope ratios of the first metal, second metal, and third metal to form a multiple metal isotope signature, wherein the multiple metal isotope signature comprises bulk concentrations and compound specific metal isotope ratios;
(f) using the multiple metal isotope signature to determine one or more of type of hydrocarbon in the subsurface accumulation, quality of hydrocarbon in the subsurface accumulation, and source of the hydrocarbon; and
(g) developing or refining a hydrocarbon exploration, hydrocarbon development, or hydrocarbon production strategy based on the determined one or more of type of hydrocarbon, quality of hydrocarbon, and source of the hydrocarbon.

2. The method of claim 1, wherein the sample comprises produced fluids from the well.

3. The method of claim 1, wherein the sample comprises hydrocarbons.

4. The method of claim 1, wherein the first metal, second metal, and third metal are selected from vanadium, nickel, molybdenum, chromium, iron, cobalt, zinc, and copper.

5. The method of claim 1, wherein at least one of the first metal, second metal, and third metal are selected from vanadium, nickel, and molybdenum.

6. The method of claim 1, wherein the first metal is vanadium, the second metal is nickel, and the third metal is molybdenum.

7. The method of claim 1, wherein at least one of the first, second, and third metals is vanadium and the multiple metal isotope signature comprises a ratio of $^{51}V$ to $^{50}V$.

8. The method of claim 1, wherein at least one of the first, second, and third metals is nickel and the multiple metal isotope signature comprises a ratio of $^{60}Ni$ to $^{58}Ni$.

9. The method of claim 1, wherein at least one of the first, second, and third metals is molybdenum and the multiple metal isotope signature comprises a ratio of $^{98}Mo$ to $^{96}Mo$.

10. The method of claim 1, wherein integrating the isotope ratios of the first, second, and third metals comprises forming a ternary plot of the metal isotope ratios.

11. The method of claim 1, further comprising comparing the measured multiple metal isotope signature to a database of known multiple metal isotope signatures to determine the source of the hydrocarbons in the sample.

12. The method of claim 1, further comprising developing a multiple metal isotope signature for a second sample and comparing the multiple metal isotope signature of the first sample and the second sample.

13. The method of claim 1, wherein the method further comprises integrating the multiple metal isotope signature with one or more of a multiply substituted isotopologue signature, clumped isotope signature, or position-specific isotope signature.

14. A method of producing hydrocarbons comprising:
(a) obtaining one or more samples comprising hydrocarbons;
(b) analyzing the sample to determine a geochemical signatures of the sample, wherein the geochemical signature comprises one or more of bulk metal concentration, non-metal isotopic signatures, molecular geochemistry, clumped isotope/position specific isotope geochemistry;
(c) separating metal containing components of the sample into fractions for metal isotope analysis;
(d) analyzing the fractions to determine a ratio of at least two isotopes of a first metal, a ratio of at least two isotopes of a second metal, and a ratio of at least two isotopes of a third metal;

(e) integrating the isotope ratios of the first metal, second metal, and third metal to form a multiple metal isotope signature comprising bulk concentrations and compound specific metal isotope ratios;

(f) integrating the geochemical signature and the multiple metal isotope signature; and (g) using the integrated signature to develop or refine a hydrocarbon exploration, development, or production strategy.

15. The method of claim 14, wherein the first metal, second metal, and third metal are selected from vanadium, nickel, molybdenum, chromium, iron, cobalt, zinc, and copper.

16. The method of claim 14, wherein at least one of the first metal, second metal, and third metal are selected from vanadium, nickel, and molybdenum.

17. The method of claim 14, wherein the first metal is vanadium, the second metal is nickel, and the third metal is molybdenum.

18. The method of claim 14, wherein at least one of the first, second, and third metals is vanadium and the multiple metal isotope signature comprises a ratio of $^{51}V$ to $^{50}V$.

19. The method of claim 14, wherein at least one of the first, second, and third metals is nickel and the multiple metal isotope signature comprises a ratio of $^{60}Ni$ to $^{58}Ni$.

20. The method of claim 14, wherein at least one of the first, second, and third metals is molybdenum and the multiple metal isotope signature comprises a ratio of $^{98}Mo$ to $^{96}Mo$.

21. The method of claim 14, wherein integrating the isotope ratios of the first, second, and third metals comprises forming a ternary plot of the metal isotope ratios.

22. The method of claim 14, further comprising comparing the measured multiple metal isotope signature to a database of known multiple metal isotope signatures to determine the source of the hydrocarbons in the sample.

23. The method of claim 14, further comprising developing a multiple metal isotope signature for a second sample and comparing the multiple metal isotope signature of the first sample and the second sample.

24. The method of claim 14, wherein the method further comprises integrating the multiple metal isotope signature with one or more of a multiply substituted isotopologue signature, clumped isotope signature, or position-specific isotope signature.

* * * * *